United States Patent [19]

Cupler, II

[11] 4,002,169
[45] Jan. 11, 1977

[54] METHOD AND APPARATUS FOR PERFORMING SURGERY WITHOUT TISSUE INCISION

[76] Inventor: John A. Cupler, II, 10 Cupler Drive, LaVale, Cumberland, Md. 21502

[22] Filed: Apr. 18, 1972

[21] Appl. No.: 245,121

[52] U.S. Cl. .............................. 128/276; 128/305
[51] Int. Cl.² ................... A61M 1/00; A61M 7/00; A61B 17/32; A61F 9/00
[58] Field of Search ................ 128/305, DIG. 26; 408/59

[56] References Cited
UNITED STATES PATENTS

| | | | |
|---|---|---|---|
| 291,568 | 1/1884 | Borchardt | 408/59 X |
| 589,576 | 9/1897 | Rickey | 408/59 |
| 1,208,164 | 12/1916 | Kelly | 408/59 |
| 2,850,007 | 9/1958 | Lingley | 128/305 UX |
| 3,055,370 | 9/1962 | McKinney et al. | 128/305 X |
| 3,659,607 | 5/1972 | Banko | 128/305 |
| 3,732,858 | 5/1973 | Banko | 128/305 X |
| 3,736,938 | 6/1973 | Evvard et al. | 128/305 |

Primary Examiner—Channing L. Pace
Attorney, Agent, or Firm—Colton & Stone, Inc.

[57] ABSTRACT

The introduction of surgical instruments into an animal body is effected, without tissue incision, by migrating a specially constructed hollow needle into the body behind a rotary augering tool journalled in the hollow needle. Surgical procedures may then be performed with the rotary tool or the same may be withdrawn from the in situ needle and different surgical implements substituted therefor which may be extended beyond the open end of the needle, as required. In the case of unwanted tissue removal, such as blood clots, cataracts and the like; a rotary masticating tool may be brought to the operative site by introduction through the hollow needle, the unwanted tissue masticated or liquefied and the same withdrawn through the needle bore following removal of the masticating tool. Similarly, fluids may be injected into the body and withdrawn therefrom, as required, through the hollow needle.

The application of the foregoing procedures to cataract surgery makes it possible to remove a cataract while leaving the lens capsule in place. Following removal of the cataract and total contents of the lens capsule, the volume of removed material is then replaced with a compatible lens filler material having a desired refractive index, such as silicone, and the refractive property of the lens is retained obviating the usual massive optical corrections previously associated with cataract surgery.

4 Claims, 18 Drawing Figures

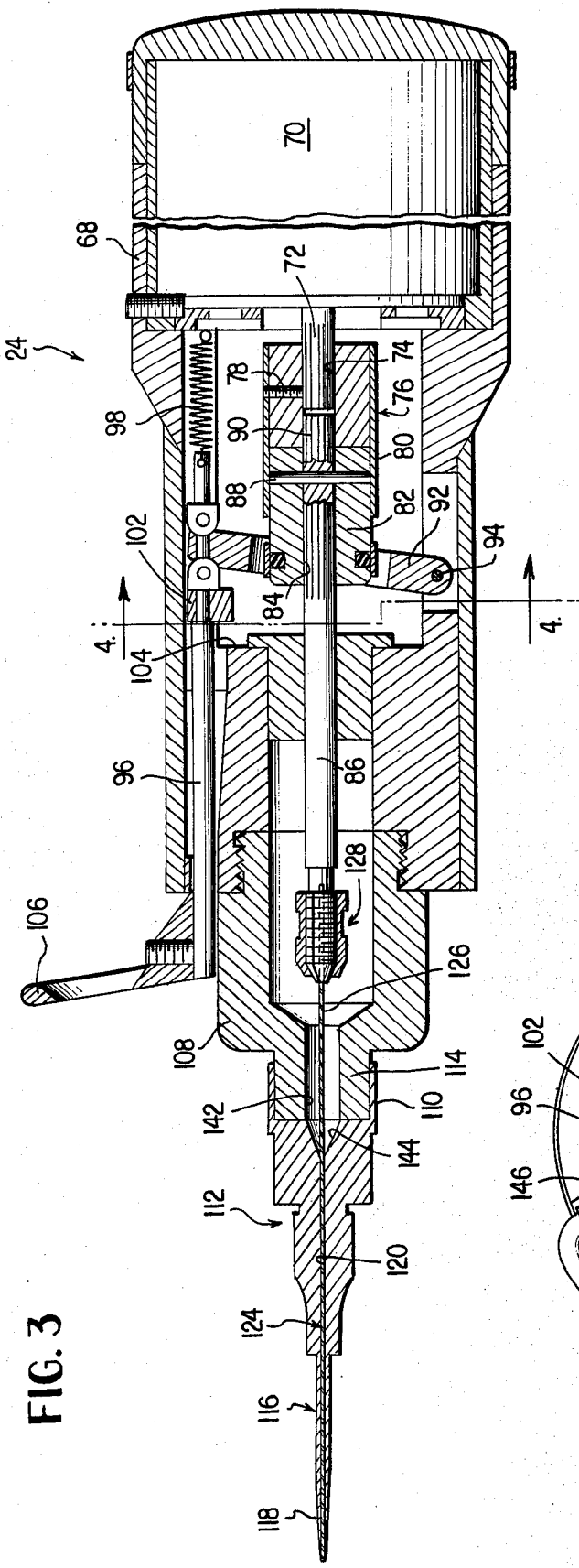
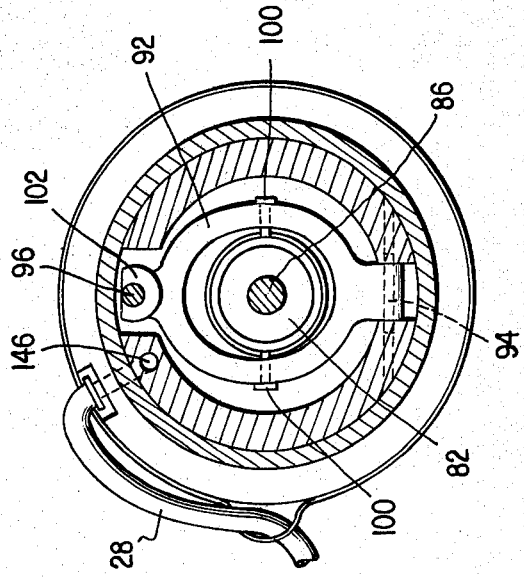

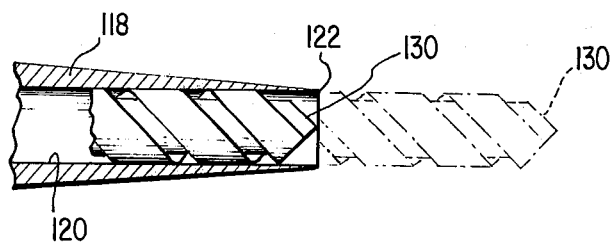
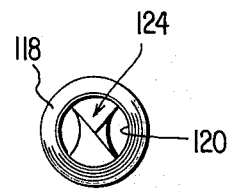
FIG. 6  FIG. 7
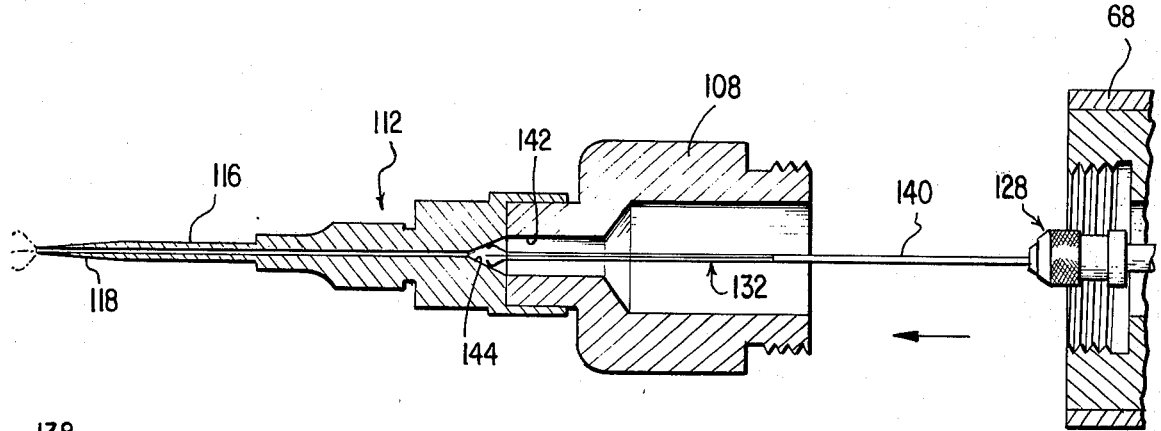
FIG. 9
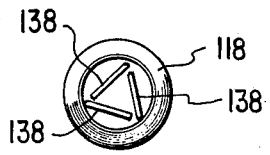
FIG. 10
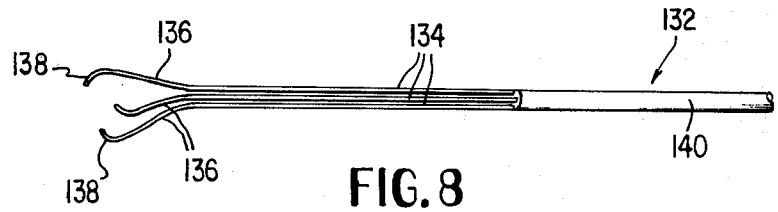
FIG. 8
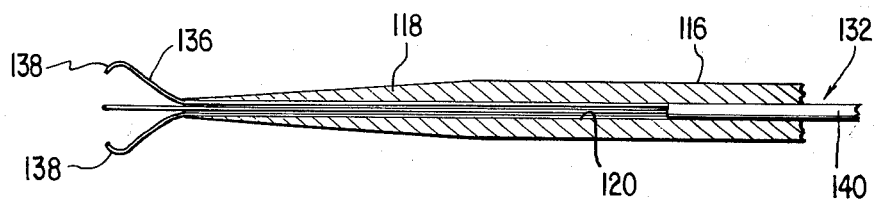
FIG. 11

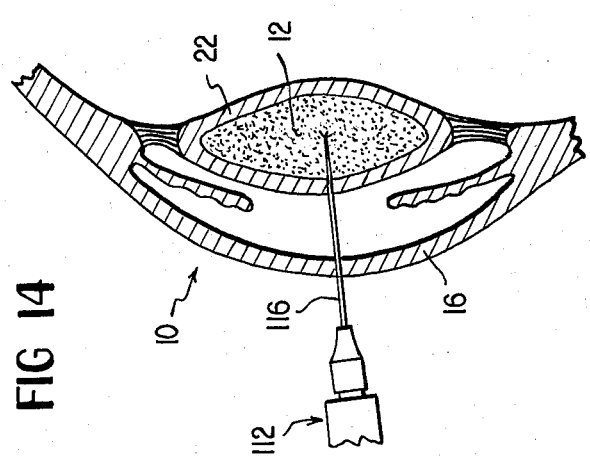
FIG. 14
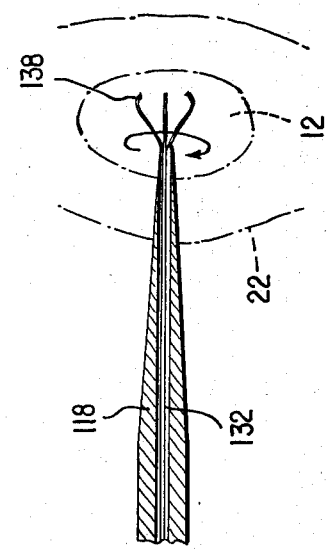
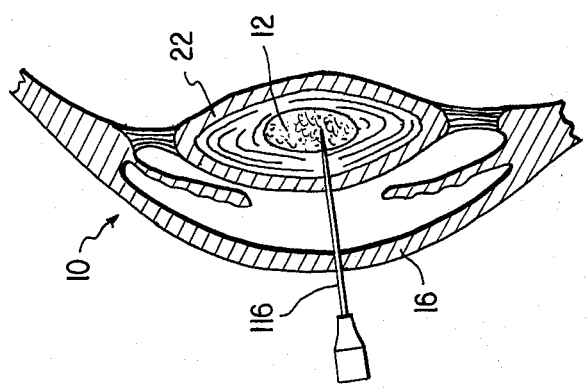
FIG. 13
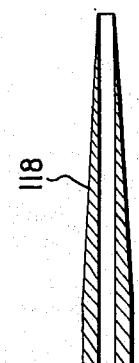
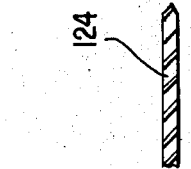
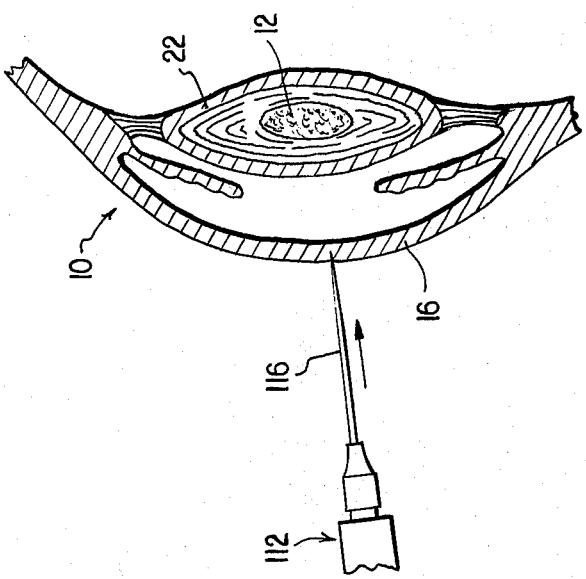
FIG. 12
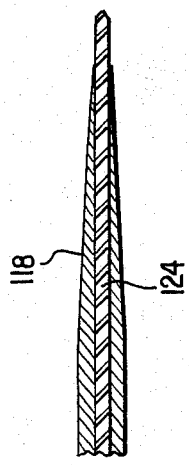

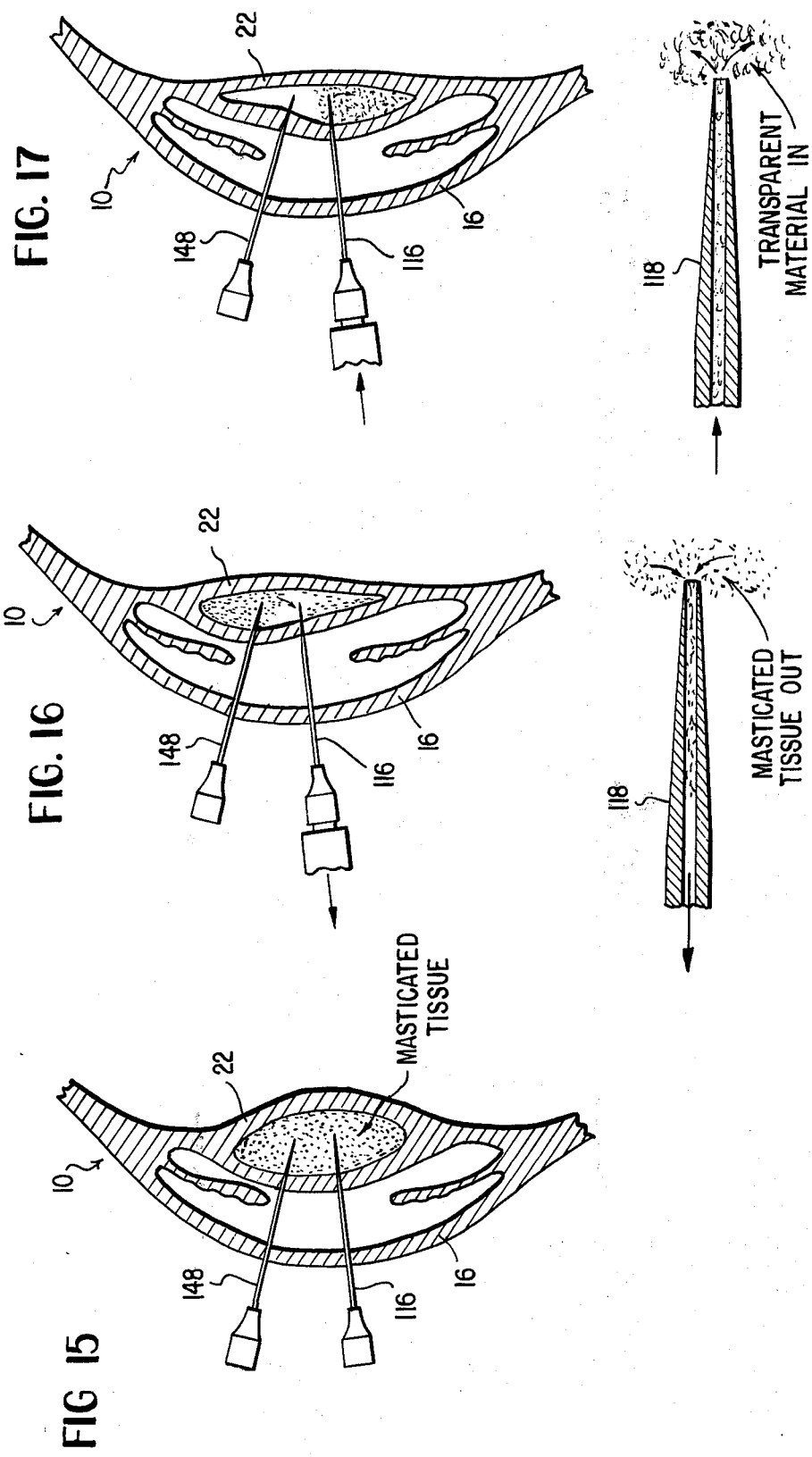

METHOD AND APPARATUS FOR PERFORMING SURGERY WITHOUT TISSUE INCISION

BACKGROUND OF THE INVENTION

Interior surgical procedures have, in the past, required surgical incisions to expose the operative area. In those instances where the operative area may be directly viewed, as through transparent tissue in the case of eye surgery, or accurately calculated, such as in stationary blood stream clots; the requirement for a surgical incision is not one of viewing but of obtaining instrument access to the area. The invention is particularly applicable to eye surgery and makes possible a new approach to cataract removal, i.e. retention of the crystalline lens capsule. Accordingly, it is this specific application of the invention which has been chosen for illustration and description.

Cataract removal from the human eye, whether in an advanced stage of opacity or at an earlier point in time before the optical fiber discoloration or clouded portion has extended throughout the lens, is normally regarded as major eye surgery requiring a substantial corneal incision of approximately 180° to provide access to the lens and cataract. The lens capsule and its contents, including the cataract, are then excised from the eye. Patient recovery times from such surgical procedures are long, as in the nature of a week; heavy optical corrections are required to supplant the function of the removed crystalline lens; and the incidence of patient satisfaction is discouragingly low. The long patient recovery time is primarily for healing of the massive corneal incision which healing process is inherently slower than most other parts of the human body because of a relatively low corneal vascular supply. Additionally, patients undergoing cataract surgery are, for the most part, elderly which further contributes to a long recovery period. Heretofore, once a cataract has developed, a patient has been confronted with only one of two choices, viz. major surgery which, if successful, will require substantial optical correction for even partial restoration of vision; or a lifetime of impaired vision.

Direct penetration of the cornea with a small surgical tool to reach the lens at first appeared to offer a reasonable alternative to the massive incision previously required. It was hypothecated that if a small hypodermic needle could be inserted to reach the interior of the lens capsule, a small rotating or vibratory tool might be inserted through the needle to masticate the cataract along with the remainder of the lens capsule contents (cortex and nucleus) to be followed by withdrawal of the tool and suction of masticated tissue through the needle while leaving the lens capsule intact to be refilled with an appropriate filler material to restore the original lens function. Theoretically, this approach would appear feasible but for the particular anatomical structures of the cornea and lens capsule through which such a needle must be inserted. Each of the cornea and lens capsule through which the needle must be inserted is so constructed as to practically assure that needle penetration may not be effected with accuracy or without great trauma to the patient. The cornea, itself, offers an almost impenetrable barrier by virtue of the very thick cellular stratum known as the substantia propria which lies just beneath the corneal epithelium. The substantia propria is comprised of approximately sixty flattened, superimposed lamellae which are made up of modified connective tissue. The fibers of each individual lamella are generally parallel with one another but at right angles to those of the next adjacent lamellae and the fibers of all the lamellae are generally directly continuous with the scleral fibers. This fibrous construction of the substantia propria provides one of the toughest and most unyielding tissues in the human body. Efforts to penetrate the substantia propria portion of the cornea, without restraining the eyeball in some manner, have proved to be impossible with even the smallest needle. Indeed, the eyeballs of experimental animals have been forced from their sockets by determined, unsuccessful efforts to force a needle through the cornea. It has been possible to penetrate the cornea by rigidifying the eyeball prior to the attempted penetration but this has involved the introduction of clamps directly into the eyeball which induces trauma at least roughly equivalent to the conventional cataract incisions.

Even if the cornea could be practically penetrated either by direct insertion of a hypodermic needle or by introducing the same through a small surgical incision, as will be discussed infra, any attempt to penetrate the lens with accuracy of location is rendered virtually impossible by the "floating" nature of the same. Although the lens capsule (capsula lentis) does not possess the same unyielding character as the substantia propria, it is highly elastic so that it does offer substantial resistance to penetration and this fact coupled with the suspensory mounting of the lens from the ciliaris muscle via the suspensory ligaments (*Zonula Ciliaris*) insures that the lens body will move upon contact so that lens penetration, if effected at all, is likely to be at a point remote from the intended location.

Thus, from the foregoing, it is apparent that any attempted direct penetration into the crystalline lens in a manner productive of less trauma than conventional cataract surgery is doomed to failure.

It was next thought that a small incision might be made through the cornea and lens capsule to permit the introduction of a small tool into the lens body. This approach, while more feasible than the conventional massive incision, yet does involve an incision which was the thing sought to be avoided by direct penetration as with a hypodermic needle. Even when such a small incision is made through the cornea, the problem of penetrating the "floating" lens yet remains unless it, too, is to be incised. The size of the incision is, of course, a direct function of the tool size to be used in removing the cataract which, if of any substantial size, will dictate an incision which may produce trauma comparable to that of conventional cataract surgery.

In the utilization of small vibrating probes to masticate or liquefy the cataract, the benefits of a small incision in the cornea are frequently offset by additional trauma introduced by the vibrating probe, itself, in the form of tissue damage by heat generation and lack of precise control in that portion of the eye to be subjected to the vibratory effects. An even greater limitation imposed by the introduction of a vibrating probe through an incised cornea and lens is that the structural integrity of the lens capsule is destroyed thus yet requiring total lens capsule removal as through the small corneal incision following a preliminary liquefaction and withdrawal of the lens contents.

The objectives of the invention are basically threefold:

1. To permit of tissue penetration by augering a self-closing wound;
2. To permit of surgical instrument introduction, as well as ingress and egress of treatment fluids, through the self-closing wound without further irritation to the same; and
3. To rehabilitate a cataractous lens following removal of the lens capsule contents including the cataract.

The separate utility of the first two mentioned objectives will become apparent from the ensuing discussion of the primary purpose of the invention which relates to cataract removal and involves penetration of the cornea and lens capsule, mastication of the lens capsule contents, withdrawal of the same; and replacement of the withdrawn volume with a substitute lens filler material to rehabilitate the lens and restore its refractive property.

SUMMARY OF THE INVENTION

Basically, penetration of the cornea and lens without migrating or incising the same is accomplished by "augering" a small specially constructed hollow needle through the cornea and lens capsule to reach the lens cortex as opposed to an attempted direct penetration, as with a hypodermic needle, or by performing a surgical incision. A small spiral fluted drill is closely fitted within the bore of a long tapered hollow needle and mounted for simultaneous rotation and reciprocation relative thereto. The O.D. of the distal end of the needle exceeds the O.D. of the drill by only approximately one thousandth of an inch and the drill is mounted for reciprocating movement relative thereto from a fully retracted position where the distal ends of the drill and needle present a substantially closed end on the needle to an extended position where the drill extends outwardly of the distal end of the needle. Following initial engagement of the needle with the cornea, the drill is rotated and extended slightly from the end of the needle. The drill and needle are then infed into the cornea at a lesser linear rate of travel than the linear speed of drill rotation. The drill thus augers into the eye, without removing material, and induces the needle to follow thereafter. In this latter connection, the drill does not actually pull the needle into or through the tissue as it will be apparent that the penetrating or infeeding movement of the needle is under the control of a surgeon. The drill, in effect, creates the self-closing wound through which the needle follows. The feasibility of this approach will be more readily appreciated when considering an exemplary drill diameter of 0.012 inch extending in advance of a long tapered needle whose outer diameter at the leading end is only 0.013 inch.

The augering, as opposed to tissue removal, effect of the drill is due to the resilient nature of the tissue which, in effect, flows along the drill flutes rather than being severed thereby as in the case of a harder material. The augering effect is quite analogous to that observed when "drilling" into a block of rubber with a spiral fluted drill wherein the drill will readily penetrate the rubber but rubber is not removed from the path of drill passage; rather it flows outwardly of the drill path and along the spiral drill flutes.

Although the infeed of the drill, like that of the needle, is obviously controlled by the surgeon; there is an actual force vector tending to advance the drill further into the tissue. This, of course, is due to the reaction of the resilient tissue material against the drill flutes and this tendency of the drill to work or burrow its way into the engaged tissue is important in understanding just how penetration of the cornea and lens capsule are achieved without migrating the same as is true upon attempted penetration with a hypodermic needle, for example. After the needle has penetrated the lens, the drill is withdrawn and a small expansible tool is inserted through the needle into the interior of the lens with the degree of tool expansion being limited by and as a function of its extension beyond the end of the needle. The expansible tool is then rotated to masticate the cataract as well as the cortical and nuclear portions of the lens. Following mastication the tool is withdrawn, the needle is left in place and a second drill and needle are used to penetrate the lens to provide a vent for the suction removal of the masticated lens contents. A source of vacuum is then connected to the first needle and the masticated lens contents are withdrawn. Following withdrawal, a filler substance, such as silicone, is injected through one of the needles to replace the volume of withdrawn material and both needles are removed. Due to the fact that no tissue was removed as an incident of needle penetration, both wounds are self-closing.

The operation is thus completed with virtually no trauma which is due, primarily, to the fact that only two very small self-closing wounds are inflicted upon the patient. Patient recovery time is very short, usually the same day, and restoration of vision without optical assistance is immediate.

DESCRIPTION OF THE DRAWINGS

FIG. 3 is a longitudinal section of the surgical instrument employed with the apparatus of FIG. 2;

FIG. 4 is a cross-sectional view taken along the line 4—4 of FIG. 3;

FIG. 5 is a greatly enlarged, broken, longitudinal section of the assembled hollow needle and spiral fluted drill used with the instrument of FIG. 4;

FIG. 6 is a greatly enlarged, fragmentary cross-section of the distal ends of the needle and drill shown in FIG. 5;

FIG. 7 is an enlarged end elevation taken along the line 7—7 of FIG. 5;

FIG. 8 is a perspective view of a masticating tool adapted to be positioned within the hollow needle bore in substitution for the fluted drill of FIG. 5;

FIG. 9 is a broken, longitudinal section of the needle end of the surgical instrument and associated body portion illustrating the telescopic assembly of the masticating tool and needle;

FIG. 10 is an end elevation of a fully telescoped needle and masticating tool;

FIG. 11 is a broken longitudinal section of the assembled needle and masticating tool;

FIGS. 12–17 are schematic representations of sequential steps in the performance of cataract surgery in accordance with the invention; and FIG. 18 is a perspective view of a modified spiral fluted drill which may be employed for surgical procedures without the hollow needle.

DESCRIPTION OF THE PREFERRED EMBODIMENTS

Figure 1:
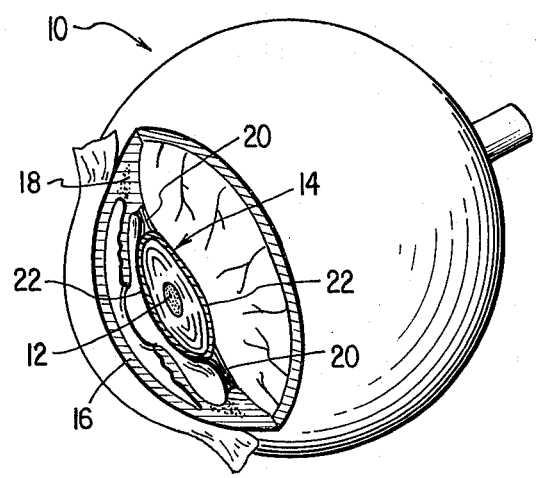
FIG. 1 is a sectioned, perspective illustration of a human eye containing an early stage cataract.

In FIG. 1 is depicted a human eye 10 displaying an early stage cataract 12 forming in the nucleus of the crystalline lens 14 which lens is suspended interiorly of the cornea 16 from the ciliaris muscle 18 via suspensory ligaments 20. The primary purpose of the invention is to obtain access to the interior of lens capsule 22 and remove the entire contents thereof including the cortex, nucleus and cataract without incising the cornea or destroying the structural integrity of the lens capsule so that the same may be rehabilitated to restore the original lens function. The apparatus for achieving this function is detailed in FIGS. 2–11. A secondary procedure involves flushing out the lens capsule with a sterile solution and then drying the same with a sterile gas prior to the replacement of the removed tissue with a lens filler material having a desired refractive index.

Figure 2:
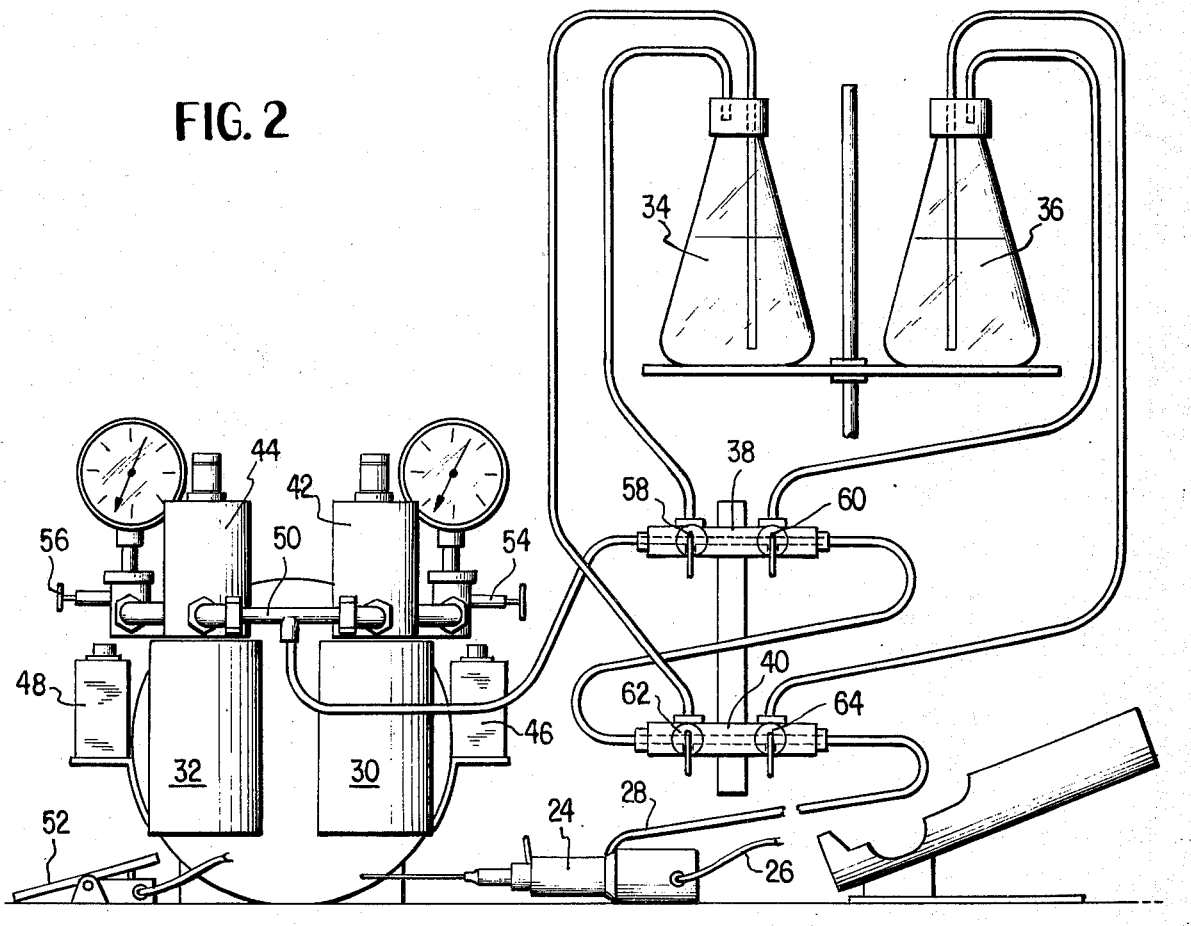
FIG. 2 illustrates exemplary equipment which may be employed to perform cataract surgery in accordance with the invention.

The basic equipment for performing cataract surgery in accordance with the present invention is shown in FIG. 2 and includes a hand held instrument 24 to which is connected flexible leads 26, adapted for connection to a source of electric power (not shown), and a flexible fluid conduit 28. Conduit 28 is adapted for the selective communication of instrument 24 with any of a vacuum source 30, a sterile gas pressure source 32, a sterile cleaning solution 34 and a fluid lens filler material 36 via valve manifolds 38, 40 and appropriately interconnected conduits. Solenoids 42, 44 whose energization times are dictated by selective settings of millisecond timers 46, 48, respectively, control the application of vacuum and pressure to pump manifold 50 in accordance with the position of the foot control pedal 52. Precise control of the vacuum and pressure sources that may be applied to pump manifold 50 by operation of foot pedal 52 may be manually effected by manipulation of restriction valves 54, 56. Pending a subsequent detailed description of the method of operation; suffice to say at this point that selective admission of vacuum, pressure, cleaning solution and lens filler material to the instrument connected conduit 28 may be controlled by the selective manipulation of three-way valves 58, 60 and 62, 64 in valve manifolds 38, 40, respectively.

The hand held instrument 24 (FIG. 3) includes a hand held body portion 68 housing, at one end thereof, a D.C. motor 70 whose splined output shaft 72 is secured within the splined bore 74 of a female coupling 76 by a set screw 78. Female coupling 76 includes an outer guide shell 80 within which is slidably received a male coupling 82 having a splined bore 84 concentric with the splined bore 74. A rearwardly splined collet drive shaft 86 extends through the splined bore in the male coupling member with the splined end 90 thereof extending into the splined bore 74 in the female coupling. A yoke 92 is fulcrummed on pivot pin 94 for limited oscillatory movement under the opposed influences of a manual control rod 96 and a return tension spring 98. Pivot pins 100 (FIG. 4) interconnect yoke 92 with male coupling 82 while a stop 102, secured to manual control rod 96, limits permissible forward (leftward as viewed in FIG. 3) movement of collect drive shaft 86 to that range of movement defined by the relative position of stop shoulder 104. Thus it will be apparent that manipulation of finger control 106, rigid with rod 96, controls the position of collet drive shaft 86 over that range of movement defined between the coaction of stop 102 and shoulder 104 on the one hand and a stop defined by abutting engagement of the coupling members 76, 82 (as in the position of FIG. 3) on the other. This limited reciprocal movement of collet drive shaft 86 is accommodated by the telescoping connection of male coupling 82 with the shell 80 of the female coupling and that end of collet drive shaft 86 which extends into splined engagement with female coupling bore 74. The permissible range of collet drive shaft movement does not, of course, exceed the length of the end 90 of shaft 86 which is received within female coupling bore 74 in the fully retracted position of FIG. 3.

The forward end of instrument 24 includes a needle adapter 108 removably screwed into instrument body 68 and the sleeved rear end 110 of a special hollow needle assembly 112 is removably fitted over a forward necked down end 114 thereof. Needle assembly 112 terminates at its forward end in a needle 116 having a long tapered end 118. The length of the tapered end portion 118 of needle 116 substantially exceeds the depth of penetration anticipated for a particular surgical operation and tapers down to a wall thickness of not more than 0.001 inches surrounding the hollow interior bore 120 at the forward or penetrating end thereof. The penetrating end of the needle terminates in a single plane lying transverse to the needle axis and is sharpened to a razor edge to present, at the forward end of the needle, a sharp annular cutting edge 122. A long spiral fluted drill 124 having an O.D. of approximately 0.001 inches less than the I.D. of needle bore 120 is telescoped therein with the shank portion 126 thereof chucked in collet 128 rigid with collet drive shaft 86. In the fully retracted position of FIG. 3 (spring 98 biasing the male coupling 82 into abutting engagement with female coupling 76), the point of tapered cutting edges 130 on drill 124 extend just to the plane of annular cutting edge 122 at the end of needle 116 while the spiral fluted portion of the drill is fully telescoped within the needle to substantially close the outer end thereof as will be apparent from FIGS. 5–7.

A rotary tool 132 (FIG. 8) having expansible masticating prongs is adaptd to be substituted for drill 124 within the bore of needle 116. Rotary tool 132 is formed from a plurality of stainless steel wires 134, one of whose terminal end portions 136 are bent and hardened, first, along a long radius away from the wire axis and then rearwardly along a short radius defining inturned ends 138. The other ends of wires 134 are rigidly joined in any desired manner, such as by beam welding or the like, to form a shank portion 140 to be chucked in collet 128. As will be apparent from FIGS. 3 and 9, rotary masticating tool 132 may be substituted for drill 124 while needle 116 is in operative position in the human eye. Needle assembly 112 is first grasped with a pair of forceps and instrument 24 is withdrawn from telescoping engagement with needle assembly sleeve 110 which may comprise either a friction fit with end 114 of needle adapter 108 or a bayonet or other interlocking engagement. Withdrawal of instrument 24 from needle assembly 112 results in the removal of drill 124 from the needle bore since the drill is still chucked in the instrument collet. Thereafter, a second instrument 24 having a rotary masticating tool 132 chucked therein may be substituted for the original instrument 24 or rotary tool 132 may be substituted for the drill and the instrument reengaged with the needle assembly. Assuming the second mode of operation using the same instrument, needle adapter 108 is unscrewed from the instrument body, collet 128 is loosened and drill 124 is removed.

The shank 140 of masticating tool 132 is then chucked in collet 128 and the spread prongs 136 are introduced into the bore 142 of needle adapter 108 which bore diameter exceeds the spread diameter of prongs 136 (FIG. 9). Further movement of the instrument and masticating tool 132 along bore 142 in the direction of the arrow from the position of FIG. 9 results in the prongs being deflected into substantially coaxial alignment with the axes of their respective wires as the extreme bent ends of the prongs engage cam wall 144 which merges the large needle adapter bore 142 with the small needle bore 120. The extreme inturned ends 138 of prongs 134 have, in the case of the stated exemplary parameters, a length of approximately 0.010 inch which permit the same to be accommodated in a generally equilateral triangular configuration within needle bore 120 as shown in FIG. 10. The masticating tool may now be run down to the end of the needle as a function of joining body portion 68 with needle adapter 108 as schematically indicated in FIG. 9; alternatively, needle adapter 108 may first be screwed onto housing 68 and the masticating tool introduced into the enlarged cam entry portion 144 of the in place needle assembly. With the instrument and needle assembly fully engaged, as in FIG. 3, the inturned prong ends 138 are substantially coplaner with annular cutting edge 122 at the distal end of the needle. Manipulation of finger lever 106 then results in a selective exposure of the prongs 136 beyond the end of needle 116 with their inherent expansion being a direct function of their exposure beyond the needle end as illustrated in FIG. 11. One purpose of the inturned ends 138 on masticating prongs 136 is to insure that the outer periphery of the prongs, as the same are rotated, do not define a sharp cutting periphery. This precludes inadvertent damage to the lens capsule should the rotating masticating tool be brought into contact with the interior surface thereof. A fluid conduit 146 formed in instrument body 68 communicates needle adapter bore 142 with flexible conduit 28 whereby needle bore 120 may be pressurized or suctioned depending upon the connection of conduit 28 to vacuum or pressure sources 30, 32.

The manner in which the apparatus, just described, may be used to remove a cataract following pupil dilation and the administration of a suitable anesthetic, preferably a local, to the patient, will be described in connection with the schematic illustrations of FIGS. 12–17 and with continued reference to FIGS. 2 and 3. In each of FIGS. 12–14, 16 and 17 an enlarged view of a needle end is separately illustrated to facilitate an understanding of the operative procedure taking place while maintaining proper perspective with the remainder of the illustrations. The instrument fitted with drill 124 is placed against the cornea with the drill being rotated by motor 70 through the splined drive connection. The drill is then extended by forward movement of finger control 106 and the instrument is moved inwardly at an infeed rate less than the linear speed drill rotation to insure that no material is removed from the eye. Motor 70 is a commercially available variable speed reversible motor having an operational range between about 5 RPM and 16,000 RPM. For the purpose of initially augering into the eye, a linear speed drill rotation just above the expected surgeon infeed speed is chosen which is well below the maximum RPM to preclude any possibility of tissue burning by frictional heat. Because of the fibrous, resilient nature of the cornea as already explained, the drill simply augers its way into the eye to form a self-closing wound and, in effect, eliminates any measurable frictional resistance to movement of the tapered needle end 118 therewith and into the self-closing wound. This first step of corneal penetration is illustrated in FIG. 12. After passing through the cornea, the lens is then penetrated in a similar manner; the augering or biting effect of the fluted drill minimizing the natural tendency of the lens to move away from the point of contact. When the needle point reaches the lens cortex; instrument body 68 is detached from needle assembly 112, body portion 68 and its interconnected drill 124 are withdrawn leaving the now hollow needle 116 in place in the eye. This is the schematic illustration of FIG. 13. Drill 124 is then released from collet 128 and masticating tool 132 is then substituted therefor. Alternatively, a second instrument body already fitted with a masticating tool may be substituted for that previously used. Instrument body 68 is then fitted back onto needle assembly 112 which results in the outer ends of prongs 136 being positioned at the end of the needle but still telescoped therein since tension spring 98 maintains the collet drive shaft 86 in the retracted position of FIG. 3. The surgeon then advances finger control 106 to extend expansible probes 136 a desired amount to masticate the entire contents of the lens capsule, including the cataract 12. It will be apparent that rotation of the probes may be accompanied by movement of the instrument and/or further expansion of the probes to liquefy or masticate the entire contents of lens capsule 22 as schematically illustrated in FIG. 14. It may, in some instances, be desirable to make several penetrations with the drill to avoid excessive movement of the needle within the cornea and lens capsule. In either event, once the contents of the lens capsule has been masticated as schematically indicated in FIG. 14; the instrument body is again removed from the needle assembly leaving the same in place. A second needle 148, fitted with a spiral, fluted drill, is then augered into the now masticated lens cortex and the drill withdrawn. This is the operating stage of FIG. 15 where two spaced hollow needles are in communication with the masticated tissue. An instrument body 68 is then reconnected to one of the hollow needles, three way valves 58, 60, 62, 64 in valve manifolds 38, 40 are positioned as in FIG. 2, and solenoid 42 is activated by toe depression of foot pedal 52 to apply suction to one needle bore 120, via conduit 28 to withdraw the masticated lens capsule contents, as indicated in FIG. 16, with the other of the two needles acting as a suction vent. The duration and magnitude of the applied suction are automatically controlled by the preset millisecond timer 46 and restriction valve 54.

Following the suction removal of the lens capsule contents, the lens capsule is to be flushed, dried and refilled with an appropriate lens filler material. Although a separate sterile set-up of the type shown in FIG. 2 might be brought into use at this point; the following description assumes the use of the same equipment throughout the various surgical procedures in order to provide a more complete description.

Recalling that both hollow needles are still in place within the eye, and one instrument body is connected to one of the needle assemblies; three way valve 58 is rotated clockwise 90°, three way valve 62 is rotated counter clockwise 90° and pressure control solenoid 44 is activated by heel depression of foot pedal 52 to pump cleaning solution through the interconnecting conduits, including conduit 28, downstream of the cleaning solution and into lens capsule 22 from which the excess fluid vents through the vent needle. Three way valve 58 is then returned to the position of FIG. 2, three way valve 62 is rotated 90° clockwise from the position of FIG. 2 and suction is applied by activation of solenoid 42 to draw cleaning solution through those conduit connections not cleaned during the initial flushing of lens capsule 22. All of the three way valves are then positioned as in FIG. 2 and solenoid 44 is activated to pump sterile gas through the main line conduits interconnecting pump manifold 50 and the instrument connected conduit 28. This gas pressure provides an additional flushing action for the lens capsule as the remaining cleaning fluid in the conduits downstream of the cleaning solution is forced through the lens capsule and out the vent or bleed needle. The pressurization with sterile gas is continued until the lens capsule 22 is dry and sterile.

Three way valve 60 is then rotated clockwise 90° from the position of FIG. 2 and three way valve 64 is rotated 90° counter clockwise from the FIG. 2 position. Solenoid 44 is then activated to pump lens filler material 36 into the lens capsule as indicated in FIG. 17. Following the expansion of lens capsule 22 with a desired volume of filler material, such as silicone for example, accompanied by a bleed of any excess material through the bleed needle; both needles are withdrawn, the wounds are self-closing and the operation is complete.

Although a hollow needle has been described as one means of affording instrument entry into a body in connection with cataract surgery where multiple connections to the hollow member are required, it is apparent that in simpler surgical procedures the needle could be dispensed with and instrument entry effected directly with a hollow drill. Thus, in removing a small blood clot, for example, penetration could be effected by augering as already described with a hollow, spiral fluted drill 150 (FIG. 18) chucked in collet 128 and needle adapter 112 removed from instrument body 68. The drill would next be unchucked from the instrument body as by unscrewing adapter 108 to gain access to collet 128. A tool similar to the masticating tool 132 could then be run down the drill bore 152 to reach the interior operative location. If the surgeon merely wished to grasp the small clot and withdraw the same through the hollow drill (it being understood that the drill dimensions are selected to accommodate the size clot anticipated) it would be unnecessary to chuck the grasping tool since it could be manually manipulated to spread the prongs and then contract the same to grip the clot by withdrawal of the gripping tool into the hollow drill bore. Similarly, the masticating tool could be chucked for rotation, and the clot masticated and withdrawn generally in the manner described for cataract surgery.

Additionally, the hollow drill 150 may be advantageously used for substantially any function presently performed by a hypodermic needle such as withdrawing blood or other body fluids and in the administration of simple injections. Examplary of the foregoing is the frequently experienced difficulty of blood withdrawal from a small veined person; the small vein tending to move away from or be deflected by the needle point. In such cases it is not unusual to do several needle punctures before the vein is penetrated. The augering effect of the drill minimizes this tendency for the vein to deflect as the spiral flutes come into biting contact with the vein almost simultaneously with initial contact. Once the vein is penetrated, the instrument body may be detached and a withdrawal syringe connected to the in place hollow drill which then performs the function of a hollow needle. More desirably, however, the instrument body would be fitted with a self contained syringe.

When using the hollow drill 150 it will normally be desirable to reverse the rotational direction of the drill to facilitate withdrawal.

I claim:
1. A method of removing cataracts, comprising; migrating a hollow needle into an organic eye and into the interior of the crystalline lens capsule containing a cataract; inserting a contractible and expansible masticating tool into said hollow needle in the contracted condition thereof; advancing the contracted masticating tool to the open end of the hollow needle in the interior of the crystalline lens capsule; advancing the masticating tool beyond the open end of the hollow needle and expanding the same within the crystalline lens capsule into masticating contact with the lens contents; rotating the expanded masticating tool and masticating the entire contents of the lens capsule including the cortex, nucleus and cataract while maintaining the structural integrity of the lens capsule; and withdrawing the masticated material through said hollow needle.

2. A method of cataract surgery, comprising; inserting an augering tool through the bore of a hollow needle; rotating said augering tool and extending the same from one end of the needle; infeeding the needle and augering tool into an organic eye and into the interior of the crystalline lens capsule containing a cataract; retaining said needle in place within the eye and removing the said augering tool; inserting a contractible and expansible masticating tool into said hollow needle in the contracted condition thereof; advancing the contracted masticating tool to the open end of the hollow needle in the interior of the crystalline lens capsule; advancing the masticating tool beyond the open end of the hollow needle and expanding the same within the crystalline lens capsule into contact with the interior contents of the crystalline lens capsule; rotating the expanded masticating tool to masticate the lens capsule contents; retaining said needle in place and withdrawing said masticating tool; infeeding a second needle and augering tool into said eye and into said lens capsule; retaining said second needle in place and withdrawing said second augering tool; and withdrawing the masticated contents of said lens capsule through one of said hollow needles.

3. The method of claim 2 including the additional step of replacing the volume of the withdrawn lens contents through one of said hollow needles.

4. A method of removing cataracts, comprising; migrating a hollow needle into an organic eye and into the interior of the crystalline lens capsule containing a cataract; the step of migrating said hollow needle including rotating a rotary augering tool within said hollow needle and concomitantly advancing said rotary augering tool and hollow needle into said eye with said rotary augering tool in advance of said hollow needle; withdrawing said rotary augering tool from said needle while maintaining said hollow needle in place within said eye; inserting a contractible and expansible rotary masticating tool into said hollow needle in the contracted condition thereof; advancing the contracted masticating tool to the open end of the hollow needle in the crystalline lens capsule; advancing the masticating tool beyond the open end of the hollow needle and expanding the same within the crystalline lens capsule into masticating contact with the lens capsule contents; rotating the expanded masticating tool and masticating the entire contents of said lens capsule including the cortex, nucleus and cataract while maintaining the structural integrity of the lens capsule; withdrawing the masticated material through said hollow needle; and refilling the lens capsule.

\* \* \* \* \*